United States Patent
Granqvist et al.

(10) Patent No.: US 10,313,420 B2
(45) Date of Patent: Jun. 4, 2019

(54) REMOTE DISPLAY (71) Applicant: Polar Electro Oy, Kempele (FI)

(72) Inventors: Niclas Granqvist, Magenwil (CH); Mika Erkkila, Oulu (FI); Olli Komulainen, Oulu (FI)

(73) Assignee: Polar Electro OY, Kempele (FI)

( * ) Notice: Subject to any disclaimer, the term of this patent is extended or adjusted under 35 U.S.C. 154(b) by 245 days.

(21) Appl. No.: 14/917,828

(22) PCT Filed: Sep. 13, 2013

(86) PCT No.: PCT/FI2013/050889
§ 371 (c)(1),
(2) Date: Mar. 9, 2016

(87) PCT Pub. No.: WO2015/036649
PCT Pub. Date: Mar. 19, 2015

(65) Prior Publication Data
US 2016/0226945 A1    Aug. 4, 2016

(51) Int. Cl.
*H04L 29/08* (2006.01)
*G06F 17/21* (2006.01)
(Continued)

(52) U.S. Cl.
CPC .......... *H04L 67/02* (2013.01); *A61B 5/02438* (2013.01); *A61B 5/681* (2013.01); *A61B 5/7435* (2013.01); *G06F 3/04842* (2013.01); *G06F 17/212* (2013.01); *G06F 19/3418* (2013.01); *H04L 67/42* (2013.01); *A61B 5/6823* (2013.01);
(Continued)

(58) Field of Classification Search
CPC ....... H04L 67/02; H04L 67/42; A61B 5/7435;
A61B 5/681; A61B 5/02438; A61B 5/7475; A61B 5/6824; A61B 5/6823; G06F 3/04842; G06F 17/212; G06F 19/3418; G06F 19/3481
See application file for complete search history.

(56) References Cited

U.S. PATENT DOCUMENTS

| | | | |
|---|---|---|---|
| 2003/0041866 A1 | 3/2003 | Linberg et al. | |
| 2008/0091175 A1* | 4/2008 | Frikart | G06F 19/3418 604/891.1 |
| 2011/0152695 A1* | 6/2011 | Granqvist | A61B 5/0006 600/481 |

FOREIGN PATENT DOCUMENTS

WO    2013/103570 A1    7/2013

OTHER PUBLICATIONS

International Search Report and Written Opinion, Application No. PCT/FI2013/050889, 10 pages, dated Dec. 6, 2013.
(Continued)

*Primary Examiner* — Chris Parry
(74) *Attorney, Agent, or Firm* — FisherBroyles, LLP (57) ABSTRACT

A system includes a portable device and an external device connected wirelessly. Graphical user interface data determines a user interface functionality to be executed in a user interface of the external device in the portable apparatus, and is transmitted to the external device. The user interface functionality includes presenting at least one graphical interaction element on the user interface and receiving user input as a response to the user interacting with the graphical interaction element. The input data received from the user interface is used in the portable device to control a computer process relating to physiological data.

19 Claims, 4 Drawing Sheets

(51) Int. Cl.
*G06F 3/0484* (2013.01)
*H04L 29/06* (2006.01)
*G06F 19/00* (2018.01)
*A61B 5/00* (2006.01)
*A61B 5/024* (2006.01)

(52) U.S. Cl.
CPC .......... *A61B 5/6824* (2013.01); *A61B 5/7475* (2013.01); *G06F 19/3481* (2013.01)

(56) References Cited

OTHER PUBLICATIONS

Search Report from the Patent Office of the People's Republic of China for Patent Application No. 2013800807870; dated Jul. 25, 2018, 2 pgs.

* cited by examiner

REMOTE DISPLAY

CROSS-REFERENCE TO RELATED APPLICATION

This application is a National Stage application of International Application No. PCT/FI2013/050889, filed Sep. 13, 2013, which is incorporated by reference herein in its entirety.

FIELD

The invention relates to the field of biometric sensing, and particularly to controlling an external device comprising a graphical user interface functionality related to physiological data presented on the graphical user interface.

DESCRIPTION OF THE RELATED ART

Biometric sensors, such as heart activity sensors and/or monitors, are commonly used during exercise by professional athletes as well as ordinary people. Biometric sensors of this type typically provide a user with information enabling an efficient workout. A typical heart activity monitoring system, for example, comprises a biometric sensor attached to the user's body and configured to measure heart activity, such as heart rate, of the user, and to transmit the measurement data to another device, such as a portable training computer. This other device receives the measurement data from the biometric sensor, processes the measurement data, and displays the processed information, such as heart rate information. The other device may also process the measurement data to calculate more advanced information, such as energy expenditure and fitness parameters of the user.

Such portable training computers may be, for instance, wrist units comprising a display and an input interface, such as buttons and/or a touch screen, and sensors without a tangible user interface. The user interface on such portable training computers is often rather limited. A major factor limiting the user interface possibilities of portable training computers and sensors is the mere size of these devices. Therefore, it is useful to consider technologies in order to eliminate the drawbacks arising from the limitation of user interfaces.

SUMMARY

According to an aspect of the present invention, there is provided an apparatus as specified in claim 1.

According to another aspect of the present invention, there is provided a method as specified in claim 12.

According to yet another aspect of the present invention, there is provided a computer program product embodied on a computer-readable distribution medium and comprising program instructions for carrying out the above-mentioned method, as specified in claim 13. According to another aspect, there is provided a computer-readable distribution medium or article of manufacture containing the above-mentioned computer program product.

Embodiments of the invention are defined in the dependent claims.

BRIEF DESCRIPTION OF THE DRAWINGS

In the following the invention will be described in greater detail by means of preferred embodiments with reference to the attached drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned, and such embodiments may also contain features/structures that have not been specifically mentioned.

Figure 1:
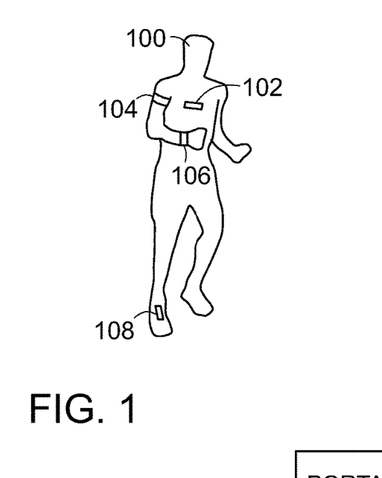
FIG. 1 illustrates equipment for physiological measurements.

FIG. 1 illustrates some exemplary equipment for physiological measurements, such as measuring exercise-related data in order to monitor a workout of a user 100, providing physiological data. Examples of physiological measurement devices and/or physiological sensor devices providing physiological data comprise sports/training computers having an integrated sensor, such as a GPS receiver or another motion sensor used for measuring speed and/or acceleration of the exercise; biosignal sensors, such as heart activity sensor and/or electromyogram (EMG) sensor; motion sensors, such as an accelerometer, a gyroscope, a stride sensor, a GPS receiver, a cadence sensor, and/or a magnetometer; biochemical sensors, such as a lactate sensor, a blood sugar sensor and/or hormone sensor, for example. It should be noted that, for example, a GPS receiver or another motion sensor used for measuring speed and/or acceleration of the exercise, such as of running or skiing, may be classified as one type of physiological sensor. In general, a physiological measurement device and/or a physiological sensor device providing physiological data may comprise any sensor or any other equipment capable of monitoring, storing and/or recording at least some exercise data related to, associated with or applied during an exercise. The physiological measurement and/or sensor devices in the embodiments are mentioned as examples only, and it is clear to a person skilled in the art that the specific device may be replaced by another physiological measurement and/or sensor device, such as a type of device described above, or a combination of such devices. Similarly, a specific physiological data mentioned in connection with an embodiment may be replaced by another type of physiological data in other similar embodiments.

Referring to FIG. 1, the user 100 may wear various devices that measure and process the physiological data, such as exercise-related data or other data related to physiological measurement. The user 100 may be provided with, for instance, the following equipment: a portable training computer or other type of a wrist unit 106, a heart activity sensor 102 worn on the chest of the user 100, a positioning device 104, and/or a stride sensor 108. Other physiological measurement accessories, not illustrated in FIG. 1, may include a bike sensor configured to measure the speed of a bike and/or a pedaling power of the user and/or a swimming sensor configured to monitor swimming motions and/or water pressure, for example. The accessories 102, 104, 108 communicate wirelessly with the wrist device 106. Various accessories may be flexibly selected to be used as needed, i.e. all of them are not necessarily needed all the time, or by all users, or in all use cases.

The heart activity sensor 102 is used for measuring the user's 100 heart activity (HA). The heart activity comprises heart rate and single channel or multichannel ECG (Electrocardiogram), for example. The heart activity sensor 102 may further measure other physiological parameters that can be measured from the user 100. Various wireless heart rate monitoring concepts exist where a heart rate sensor attached to the user's 100 chest measures the user's heart activity and transmits associated heart activity data telemetrically to a heart activity data receiver, such as the wrist unit 106 attached to the user's 100 wrist. The transmission of the heart activity data may utilize the principles of time division and/or packet transmission, for example. However, the heart rate and/or other biometric data is conventionally only measured in the heart activity sensor 102, and the measurement data is forwarded to the wrist unit 106 for further processing.

The positioning device 104 may be a receiver of a global navigation satellite system. Such a system may be the Global Positioning System (GPS), the Global Navigation Satellite System (GLONASS), the Galileo Positioning System (Galileo), the Beidou Navigation System, or the Indian Regional Navigational Satellite System (IRNSS), for example. The positioning device 104 determines its location elements, such as longitude, latitude, and altitude, using signals transmitted from satellites orbiting the Earth. Besides global navigation satellites, the positioning device 104 may also determine its location by utilizing other known positioning techniques. It is well known that by receiving radio signals from several different base stations, a mobile phone may determine its location. The positioning device 104 may utilize such schemes as well. In an embodiment of the invention, the positioning device 106 applies proprietary positioning methods based on optical or electromagnetic measurements.

The stride sensor 108 or the swimming sensor may comprise one or more motion sensors measuring the movement of the user 100, and a processing unit configured to process the measured motion data of the user 100 and/or to transmit the processed data to the wrist device 106 over a wireless connection. The motion sensor actually measures its own motion based on acceleration measurement, for example, and converts the acceleration into an electric signal. The electric signal is converted into a digital format in an AD converter. Acceleration can be expressed by the unit of measurement g. One g is the acceleration caused to an object by earth's gravity. Accelerations between −2 and +2 g can usually be measured from human movement. Various techniques may be used for measuring acceleration. Piezo-resistor technology employs material whose resistance changes as it compresses. The acceleration of mass produces a force in a piezo resistor. If a constant current is supplied through the piezo resistor, its voltage changes according to the compression caused by acceleration. In piezo-electric technology, a piezo-electric sensor generates charging when the sensor is accelerated. In silicon bridge technology, a silicon chip is etched so that a silicon mass remains on it at the end of a silicon beam. If acceleration is directed to the silicon chip, the silicon mass focuses a force on the silicon beam, thus changing the resistance of the silicon beam. Micro-machined silicon technology is based on the use of a differential capacitor. Voice coil technology is based on the same principle as a microphone. Examples of suitable movement sensors include: Analog Devices ADXL105, Pewatron HW or VTI Technologies SCA series. The implementation of the accelerometer may also be based on other appropriate techniques, for example on a gyroscope integrated into a silicon chip or on a micro vibration switch incorporated into a surface mounting component.

In summary, the accessory devices 102, 104, and 108 including heart activity sensors, bike sensors and swimming sensors, for example, each comprise at least one measurement sensor which measures some aspect of the exercise. The accessory apparatuses 102, 104, and 108 may provide raw measurement data without further processing, or the accessory apparatuses may process the raw data before outputting it. Conventional accessory apparatuses, when provided with processing capabilities, are hardwired to carry out a predetermined processing to the measured data, which is very inflexible, as their operational parameters are fixed and cannot be changed after the manufacturing process is complete.

The wrist unit 106 comprises a user interface which may comprise a display, sound producing equipment, a keyboard, and/or a keypad as well as other user interface elements known as such. The display may be a liquid crystal display, for example, but it may also be implemented by any appropriate technique. The display may also incorporate other user interaction equipment, such as touch input or haptic feedback enabling touch screen functionalities, or other user interface functionalities, to be used on the display. The sound producing equipment may comprise a loudspeaker or simpler equipment, such as a piezo element, for producing beeps or other audio signals. The keyboard/keypad may comprise a complete (QWERTY) keyboard, a mere numeric keypad or only a few push buttons and/or rotary buttons. In addition, the user interface 308 may comprise other prior art user interface elements, for example various types of cursor focusing equipment, such as a mouse, a track ball, various arrow keys or a touch sensitive area, or elements enabling audio control. A parameter relating to the exercise may be shown on the user interface 106, on the display, for example. The wrist unit 106 also comprises communication circuitry for communicating with the accessory devices 102, 104, and 108, as described in greater detail below.

Figure 2:
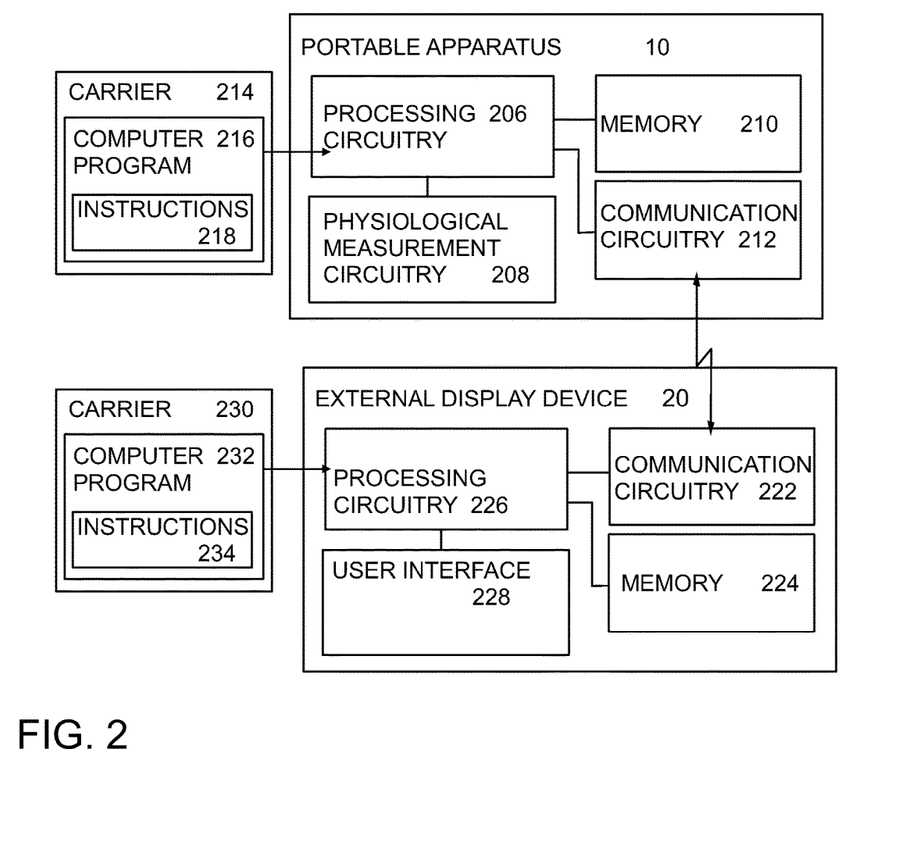
FIG. 2 is a generic block diagram of a system according to an embodiment of the invention.

FIG. 2 illustrates a generic block diagram of a system according to an embodiment of the invention. Referring to FIG. 2, an embodiment of the present invention provides a portable apparatus 10 comprising a communication circuitry 212 configured to provide the portable apparatus 10 with bidirectional wireless communication capability, a processing circuitry 206, and a memory 210.

According to an embodiment, the portable apparatus 10 may also comprise a physiological measurement circuitry 208 configured to measure physiological data related to a user 100 carrying out an exercise. The physiological data may comprise, for instance, exercise-related measurement data that is data characterizing an exercise. The portable apparatus 10 may then comprise one or several of the accessory devices 102, 104, 108 described in connection with FIG. 1 and/or other sensors, measurement units or equipment providing physiological data. According to another embodiment, the portable apparatus 10 may be configured to receive physiological data, such as exercise-related measurement data, from one or several external sensors or measurement units, such as the accessory devices 102, 104, 108 described in connection with FIG. 1. According to yet another embodiment the portable apparatus 10 may comprise a combination of the above-mentioned embodiments, in other words a combination of a physiological measurement circuitry and receiving equipment for receiving physiological data from other devices.

In an embodiment, physiological data comprises exercise-related measurement data characterizing the user's heart activity. The exercise-related measurement data may comprise a part of a single or multi-channel ECG signal in the form of a character, such as timing instant, associated with a heart pulse.

In an embodiment of the invention, the physiological data characterizes the user's 100 motion. The physiological data may comprise one- or multi-dimensional acceleration values, one- or multi-dimensional force values associated with degrees of freedom of motion, electric signal characters, such as voltage values, associated with the degrees of freedom of motion. The physiological data may also comprise advanced motion information, such as speed and/distance values which are usually provided by commercially available motion detectors. The motion may further be presented by other characteristics, such as pulses and amplitudes associated with motion. The physiological data may characterize the motion of the user's 100 limbs, such as arms or legs, or it may present the motion of the user's 100 overall motions.

The processing circuitry 206 is configured to determine graphical user interface data (GUI data) for an external device 20, and to communicate with an external device 20 over the bidirectional wireless communication connection through the communication circuitry 212 so as to cause the graphical user interface data determined in the portable apparatus 10 to be transmitted wirelessly to the external device 20. The graphical user interface data 40 may determine at least one user interface functionality to be executed in a user interface of the external device 20. The user interface functionality may comprise presenting at least one graphical interaction element 50 on the user interface and receiving user input as a response to the user interacting with the graphical interaction element 50 provided on the external device 20. The portable apparatus 10 may further be configured to control a computer process relating to physiological data with the input data received from the external device. The graphical interaction element 50 may represent physiological data, such as physiological measurement related data, for example, on the graphical user interface.

The graphical interaction element 50 is a graphical element displayed on the user interface of the external device 20. The graphical interaction element 50 is associated with a user input functionality on the user interface of the external device 20.

In an embodiment, the graphical interaction element 50 indicates at least a portion of touch interaction area provided on the user interface of the external device 20.

In an embodiment, the graphical interaction element and the touch interaction area have at least a partial overlap with each other.

In an embodiment, the touch interaction area indicated by the graphical interaction element 50 or at least partially overlapping with the graphical interaction element 50 is associated with the user input functionality associated with the graphical interaction element 50.

In an embodiment, graphical interaction element represents physiological measurement and/or an audio interaction. Some examples of physiological measurements and audio interactions are described in connection with the embodiments.

According to an embodiment, the processing circuitry 206 of the portable apparatus 10 may also be configured to receive the physiological data from an internal or external physiological measurement circuitry 208, and to process the physiological data in order to obtain advanced or "refined" physiological data.

According to an embodiment, the portable apparatus 10, preferably the processing circuitry 206 of the portable apparatus 10, is further configured to cause through the communication circuitry 212 wireless transmission of the processed physiological data to the external device 20 and to receive input data from the external device 20. The input data may define how the physiological data is processed, the type of the advanced physiological data produced, and/or how the physiological data and/or the advanced physiological data are displayed, for example. The received input data may then be stored in the memory 210 for use in the processing of the physiological data and/or determining the graphical user interface for the external device 20 and/or for the portable apparatus 10. In other words, the input data may be used as configuration data that affects how the physiological data is processed in the portable apparatus 10 and/or displayed either on the portable apparatus 10, external device 20 or both, for example. According to a further embodiment, the input data may also be forwarded, possibly after further processing, from the portable apparatus 10 to a further apparatus, such as an accessory device comprising a physiological measurement sensor, for example.

According to an embodiment, the portable apparatus 10 itself may comprise a physiological measurement device and/or a physiological sensor, such as any one of the accessory apparatuses 102, 104, and 108; a hybrid apparatus comprising a plurality of different types of physiological sensors and measurement circuitries, like a heart activity sensor, a motion sensor, and/or a positioning sensor; a portable training computer; and/or a mobile phone.

According to an embodiment, the graphical user interface data for the external device 20 is determined in response to a connection being established between the portable apparatus 10 and the external device 20.

According to an embodiment, the graphical user interface data determines at least one user interface functionality. The user interface functionality may comprise presenting at least one graphical interaction element on the user interface and/or receiving user input as response to the user interacting with the graphical interaction element. The user interface may be provided and/or the at least one graphical interaction element may be presented at least on the external device. User input may be provided on the external device as a touch screen input functionality, for example. According to an embodiment, graphical user interface data may further determine a size of a graphical interaction element, the colour mode of a graphical interaction element and/or the position of a graphical interaction element presented on the user interface.

The bidirectional communication link between the portable apparatus 10 and the external device 20 may be used to enable the portable apparatus 10 to act as a server having control over the user interface and the external device 20 to act as a client whose content is fully controlled by the portable device. In other words, the content displayed on the external device 20 is affected in response to detection of input on the external device 20, wherein the content comprises the graphical appearance of at least one graphical interaction element, the content of the graphical interaction element, the manner in which the physiological data represented by the graphical interaction element is processed or the graphical interaction element(s) and/or display segments to be displayed on the external device 20 or a combination thereof. The computer process related to the physiological data, such as a computer process related to heart activity measurement, energy expenditure, a heart rate range, and/or training load, may be executed in the portable apparatus 10 and the user input received from the external device 20 may be used to control this computer process and the updated graphical user interface data may then be transmitted wirelessly to the external device 20. This helps to provide a similar, familiar user interface on different display devices while having minimum system requirements for the external device 20. Basically almost any device that comprises any form of display equipment for displaying graphical interaction elements pushed to it, such as a basic viewer application; communication equipment, such as a communication circuitry, for establishing a bidirectional communication link with the portable apparatus 10; and the hardware and software to enable configuration of a touch screen; may be suitable for the purpose.

The bidirectional communication link between the portable apparatus 10 and the external device 20 may then be used so that user input may be given via the external device 20 to the portable apparatus 10. Thus, the most convenient external device 20 from the end user point of view may be selected at any time. For example, the end user 100 may be able to operate the portable apparatus 10 via the external device 20 during exercise and the procedure may be controlled by the portable apparatus 10 such that no program code specific to the portable apparatus or a minimum amount thereof needs to be installed on the external device 20.

According to an embodiment, the physiological data comprises user-related parameters which characterize the user 100 or are specific to the user 100. Examples of user-related parameters are name, and physiological parameters such as age, weight, height, gender, body mass index, maximum performance capacity, activity parameter, previous energy expenditure parameters and maximum heart rate.

According to an embodiment, the input data comprises exercise-guidance parameters, such as an energy expenditure target, heart rate zones, activity zones, anaerobic threshold, fitness classification identifier and/or dehydration warning limits. The heart rate or activity zones typically present limits within which a person shall exercise in order to reach a desired training effect. The fitness classification identifier characterizes the user's 100 physical condition as a maximum performance capacity (VO2max), for example.

In an embodiment of the invention, the advanced physiological data comprises heart rate distribution information. An exercise may be, for instance, divided into three heart rate zones: a first zone, a second zone and a third zone. The heart rate distribution information in this case may comprise the accumulated time the user 100 spent in each zone during the exercise, for example.

Depending on the embodiment, the external device 20 may comprise the wrist unit 106 or another corresponding user interface device worn by the user 100, a personal computer, a laptop, a personal digital assistant, a mobile phone, a display device or another computer device, for which a user interface may be configured for presenting the physiological data to the user 100 and for applying input data to the portable apparatus 10. The external device 20 comprises a communication circuitry 222 configured to provide a bidirectional wireless communication connection with the portable apparatus 10. The external device 20 further comprises a user interface 228 enabling interaction with a user 100 of the external device 20. The user interface 228 comprises a display and it may also comprise other user interaction equipment as listed above. The external device 20 further comprises a processing circuitry 226 that may be configured to communicate with the portable apparatus 10 through the communication circuitry 222 so as to receive the graphical user interface data determining the content and functionalities of the graphical user interface from the portable apparatus 10, to receive input data through the user interaction equipment and to cause transmission of the input data to the portable apparatus 10. Additionally, the processing circuitry 226 may be configured to receive processed physiological data from the portable apparatus 10 and to present the received processed physiological data to the user 100 as determined by the portable apparatus 10. According to an embodiment, the external device 20 itself does not comprise graphical user interface configuration data, but all the graphical user interface data, including data for providing at least one user interface functionality, is arranged to be pushed from the portable device to the external device 20 through the bidirectional wireless communication connection. In such an embodiment, the external device 20 may comprise only basic program code configured to provide user interface content and functionalities received from the portable apparatus 10 when executed in the external device 20 or a simple application for this same purpose. In such a case, the portable apparatus specific program code may not be needed at all. The external device 20 may further comprise a memory 224 for storing computer programs and applications comprising program code to be executed by the processing circuitry.

In an embodiment, the external device 20 may comprise several separate devices or parts, and the external device processing circuitry 226, external device communication circuitry 222 and external device memory 224 may be distributed between these devices or parts. In an embodiment, the external device 20 may comprise a general-purpose display device that provides the equipment for representing data and receiving user input, and a separate device connected to the general display device and comprising the external device processing circuitry 226, external device communication circuitry 222 and external device memory 224.

In an embodiment, the processing circuitry of the portable apparatus 10 and/or the external device 20 is implemented with an ASIC (application-specific integrated circuit), a digital signal processor, a microcontroller, or another similar controller configurable by computer programs and selected according to required processing capacity, power consumption, etc. Analogue-to-digital converters may also be needed for converting the physiological measurement output data provided by analogue sensors into a digital form. Such a digital signal processor may be configured by one or more computer programs.

An embodiment provides a computer program 232 comprising program instructions 234 which, when loaded into the external device 20, cause the external device 20 to carry out user interface and communication operations so as to present information received from the portable apparatus 10 to the user 100 and to receive user inputs and forward the user inputs as the input data to the portable apparatus 10.

An embodiment provides a computer program 216 comprising program instructions 218 which, when loaded into the portable apparatus 10, cause graphical user interface data to be determined for an external device 20; the graphical user interface data to be transmitted wirelessly to the external device 20 to provide at least one user interface functionality on the external device 20; data corresponding to user input to be received; and a computer process relating to physiological data to be controlled with the input data. The graphical user interface data may determine the user interface functionality to be executed in a user interface of an external device. The user interface functionality may comprise presenting at least one graphical interaction element on the user interface and receiving user input as response to the user interacting with the graphical interaction element, for example. According to an embodiment, the graphical user interface data may be determined in response to a connection being established between a portable apparatus 10 and an external device 20.

Any one of the computer programs 218, 232 may be in source code form, object code form, or in some intermediate form. Such a computer program 218, 232 may be stored in a memory 224, 210 or on a carrier 214, 230 which may be any entity or device capable of carrying the program to the external device 20 and/or the portable apparatus 10, respectively. The carrier 214, 230 may be a computer-readable storage medium. Besides this, the carrier 214, 230 may be implemented as follows, for example: the computer program 218, 232 may be embodied on a record medium, stored in a computer memory, embodied in a read-only memory, carried on an electrical carrier signal, carried on a telecommunications signal, and/or embodied on a software distribution medium. In some jurisdictions, depending on the legislation and the patent practice, the carrier 214, 230 may not be a telecommunications signal.

There are many ways to structure each of the programs 218, 232. The operations of the program may be divided into functional modules, sub-routines, methods, classes, objects, applets, macros, etc., depending on the software design methodology and the programming language used. In modern programming environments, there are software libraries, i.e. compilations of ready-made functions, which may be utilized by the program for performing a wide variety of standard operations.

The bidirectional wireless communication connection refers to a connection that transfers payload data to both directions, i.e. not just radio-link specific control signalling. A communication circuitry may be configured to operate a single bidirectional wireless communication link realized according to the specifications of Bluetooth or Bluetooth low energy, wireless USB (Universal Serial Bus) or Zigbee (IEEE 802.15.4). The bidirectional connection may even utilize wireless local area network (IEEE 802.11x), IP protocol and/or mobile telecommunication technology, such as GSM or UMTS. In the case of GSM and UMTS (or another mobile telecommunication system utilizing fixed public radio access network infrastructure), the user input data may be input via a text message (SMS) or through a packet radio connection, for instance GPRS, EDGE, W-CDMA, HSDPA/HSUPA, known in the field of mobile telecommunications. Furthermore, the communication may be based on a standard WWW mark-up language, such as HTML5, enabling the external device 20 to be used with a standard Internet browser or the like.

Alternatively, a bidirectional wireless communication connection may be provided, at the portable apparatus end, by at least two communication link modules, wherein a first communication link module is configured to transmit graphical user interface data and/or physiological data to the external device 20, and a second communication link module 312 is configured to receive the input data from the external device 20. Thus, the first communication link module 311 may be dedicated for transmission only, and it may be configured to carry out the transmission according to Bluetooth (or Bluetooth low energy), ANT, W.I.N.D, Zigbee, or inductive-based technology. The second communication link module 312 may be dedicated for reception only, and it may be configured to carry out the reception according to Bluetooth (or Bluetooth low energy), Zigbee, wireless USB, or any other suitable wireless communication technology.

In an embodiment, the inductive-based technology is based on at least one of the following frequencies: 27 kHz, 125 kHz, 131 kHz, 250 kHz, and below 10 kHz, such as a 5 kHz.

The use of the standard wireless technologies and protocols maximises the number of display devices that may be used as external display devices 20 and requires no modification in the portable apparatus end. According to an embodiment, internet protocol (IP) addresses are used to establish the wireless connection between the portable apparatus 10 and the external device 20. The portable apparatus 10 may be configured to act as a web server providing a web-based service and the external device 20 may be configured to connect to such web-based services using an internet protocol. The external device 20 may comprise any display device without any portable apparatus-specific modifications.

In an embodiment, a first and a second communication link module are configured to establish bidirectional wireless links, but to different external display devices 20. According to an embodiment, the portable apparatus 10 may comprise a sensor for physiological measurement and the user 100 may, for example, wear an external device 20, such as a wrist unit described above, and a headset, and the first communication link module may be configured to establish a first bidirectional wireless communication link to the wrist unit for presenting processed physiological data and for receiving the input data. The second communication link module may be configured to establish a second bidirectional wireless communication link to the headset for playing audible physiological data or other audio data and for receiving the input data. In the latter case, the headset may include a microphone and a voice-recognition algorithm to detect voice commands provided by the user 100 and to forward the voice commands to the sensor.

In another embodiment, the portable apparatus 10 may comprise a sensor for physiological measurement and the first communication link module may be configured to establish a bidirectional wireless link with a first external device 20 and the second communication link module may be configured to establish a bidirectional wireless link with a second external device 20'. The first external device 20 may comprise, for instance, a wrist unit as described above and the second display device may comprise a built-in display of a fitness machine or a tablet computer, for example. Depending on the embodiment and the display and other properties of the external devices 20, 20', the end user 100 may be able to select by means of user input the same graphical user interface and/or same functionality to be provided on both external devices 20, 20' or to select the interface and/or functionality or functionalities for each external device 20, 20' separately. According to an embodiment, different physiological data content, such as physiological data from different physiological measurements and/or accessory devices or other sources, and/or physiological data processed and/or represented in a different way, may be displayed on the first and the second external device 20 and 20', respectively.

According to a further embodiment, only one of the first and second external devices 20, 20' may be configured to provide at least one user interface functionality to enable input to be transferred to the portable apparatus 10, and a selected graphical interaction element or selected graphical interaction elements may be pushed to the other external device. In such an embodiment, the communication connection between the portable apparatus 10 and the latter external device may comprise a single direction wireless communication connection only, while the wireless communication connection between the previously mentioned external device and the portable apparatus 10 is provided as bidirectional.

Figure 3:
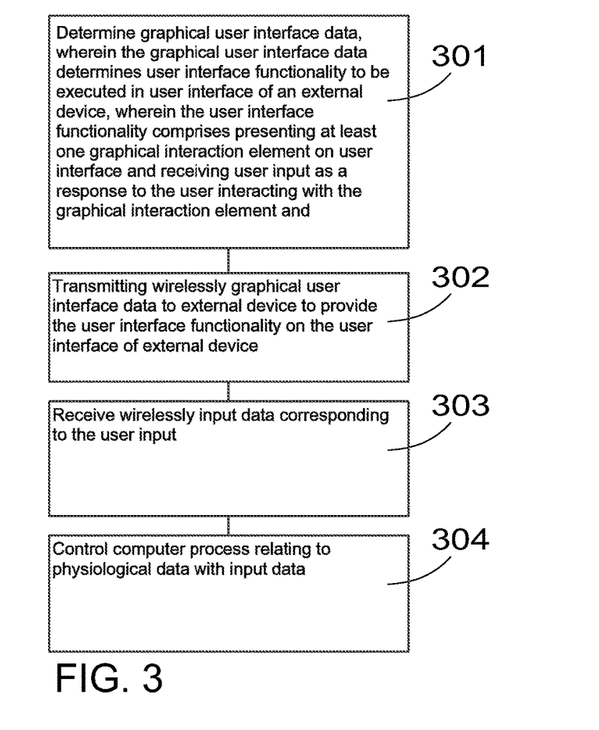
FIG. 3 illustrates schematically a method for controlling an external device 20.

FIG. 3 illustrates schematically a method for controlling an external device 20. The method may be carried out in the portable apparatus 10 according to embodiments described in this description. In the method, graphical user interface data is determined 301 for an external device 20. The graphical user interface data may determine at least a user interface functionality. This user interface functionality may be executed in a user interface of an external device and the user interface functionality may comprise at least presenting a graphical interaction element on the user interface and receiving user input as response to the user interacting with the graphical interaction element. Depending on the embodiment, several user interface functionalities may be included in the user interface data. The user interface data may, for instance, comprise several graphical interaction elements or combinations thereof, such as graphical user interface segments displayable on an external device 20 and/or several user input functionalities of different type for different control functions and/or for controlling different content, such as different physiological measurements, content and/or processing thereof, audio output or other suitable content. In an embodiment, graphical user interface data for an external device 20 may be determined 301 in response to a connection being established between the portable apparatus 10 and the external device 20.

The method further comprises transmitting 302 wirelessly the graphical user interface data to the external device 20 to provide the user interface functionality on the user interface of the external device 20. Thus, the graphical user interface data comprising at least a graphical interaction element(s) to be displayed and/or other functionalities for, for example, receiving input from an end user 100, is determined in the portable apparatus 10 and transferred to the external device 20. This means that it is not necessary to store user interface data specific to the portable apparatus in the external device 20. Thus, the portable apparatus 10 is in full control of the look and feel as well as the functionalities provided on the external device 20. This means that the similar look and feel may easily be provided on external devices 20 of all type, preferably adapted to the characteristics of each external device 20, such as size and resolution of the display, updates may be carried out simply through the portable apparatus 10 and so on.

The method also comprises receiving 303 input data corresponding to the user input received by the user interface functionality of the external device 20. The graphical user interface data determined by the portable apparatus 10 provides a graphical user interface on the external device 20 enabling the end user 100 to enter input using the user input functionalities, such as touch screen input functionalities known as such. Some of such user input functionalities are illustrated in connection with FIGS. 4 and 5, for example, but these are shown by way of example only, and it is clear to a person skilled in the art that user input and/or touch screen controls of many other type may be used as well.

The method further comprises controlling 304 a computer process relating to physiological data with the input data. The controlling may comprise the input data triggering the starting of an exercise mode, stopping an exercise mode, selecting a training program, connecting the portable apparatus 10 to a web service, providing a user identity, selecting a graphical interaction element to be displayed on the external device 20 or selecting a display segment to be displayed on the external device 20, for example.

According to an embodiment, the method further comprises transferring updated graphical user interface data to the external device 20 in response to a processed input from the graphical user interface provided on the external device 20.

The method may be carried out in a portable apparatus 10 comprising at least one memory 210 storing computer program 216 code; a communication circuitry 212 configured to provide the portable apparatus 10 with wireless communication capability; and a processing circuitry 206. The method steps may be carried out by executing the computer program code in the processing circuitry of the portable device as described.

According to an aspect of the invention, a non-transitory computer-readable medium comprises a computer program 216 for controlling a processing circuitry 206; and the computer program 216 comprises instructions 218 for execution by the processing circuitry 206 that controls an external device 20, wherein the instructions comprise the above mentioned steps.

According to another aspect of the invention, a transitory computer-readable medium comprises a computer program 216 for controlling a processing circuitry 206; and the computer program 216 comprises instructions 218 for execution by the processing circuitry 206 that controls an external device 20, wherein the instructions comprise the above mentioned steps.

According to an aspect of the invention, a computer program product is embodied on a distribution medium readable by a computer and comprises program instructions 218 which, when loaded into an apparatus 10, cause the apparatus 10 at least to carry out the above mentioned steps.

Figure 4:
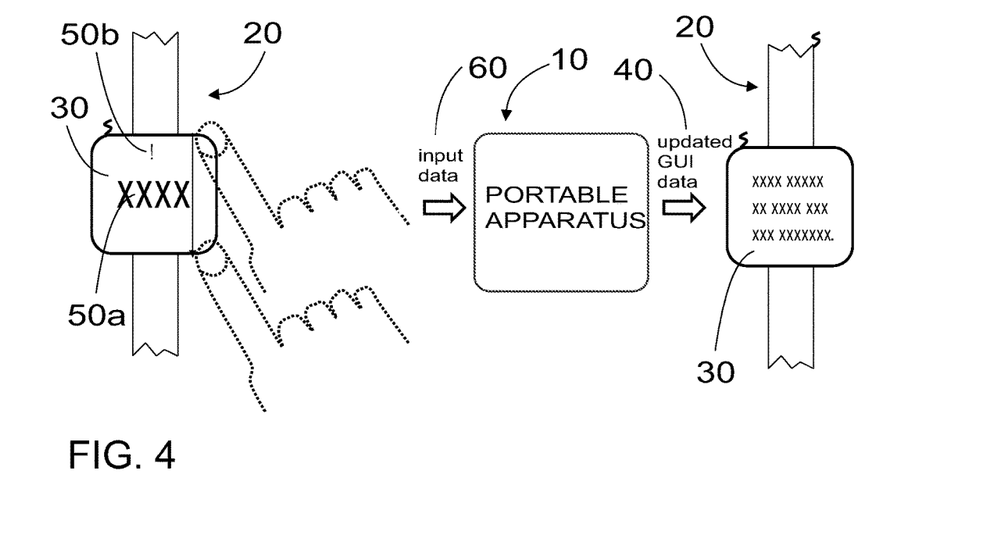
FIG. 4 illustrates entering input on an external device by a sweep touch input.

FIG. 4 illustrates schematically an embodiment, in which the external device 20 comprises a wrist unit 106. The external device 20 is provided with a user interface determined in the portable apparatus 10. A starting point is represented on the left-hand side, wherein the user interface data received from the portable apparatus 10 determines a graphical interaction element 50 to be displayed. The content of this first graphical interaction element 50a at a given moment of time is represented by "XXXX". A second graphical interaction element 50b may comprise an icon displayed on the external device 20. The icon may be arranged to vary depending on the type of the meta information, the type of available function(s) and/or on any other suitable grounds. In this example, the second graphical interaction element 50b is an exclamation point (!). Upon detecting a sweep touch input, the external device processing circuitry 226 may be configured to transfer the input data 60 to the portable apparatus 10 for processing. The portable apparatus 10 may then process the input data, control a computer process relating to physiological data with the input data, and determine and transfer to the external device 20 updated graphical user interface data 40, wherein the updated graphical user interface data affects the user interface functionality and/or the content of the user interface, such as switching from a first display view into a second display view illustrated on the right-hand side of FIG. 4, or any other suitable user interface function, in response to the input received from the external device 20.

In an embodiment, the transfer of the input data to the portable apparatus 10 may be triggered by the detection of a sweep touch input starting from a first edge of the touch-sensitive part of the display screen 30 and ending at a second edge, opposite to the first edge, of the display screen 30. The sweep touch input may start from outside the first edge of the display screen.

In an embodiment, the transfer of the input data to the portable apparatus 10 may be triggered by the detection of a sweep touch input starting from an upper edge of the touch-sensitive part of the display screen 30 and ending at a lower edge of the display screen 30, and wherein the upper edge and lower edge are determined from the viewpoint of the user 100 looking at the display screen 30. The direction of the sweep motion may thus be in parallel with a longitudinal axis of the strap 10 and/or parallel to up-down direction of text displayed on the display screen 30.

In an embodiment, the user 100 needs to start the sweep gesture outside the first edge of the display screen 30 and end it outside the opposite edge of the display screen 30 in order to ensure that the training computer detects the input. The user interface of the external device may be configured to detect the sweep touch input when it detects a touch on the first edge of the touch-sensitive part and a continuous sweep touch throughout the touch-sensitive part to the opposite edge of the touch-sensitive part.

Figure 5:
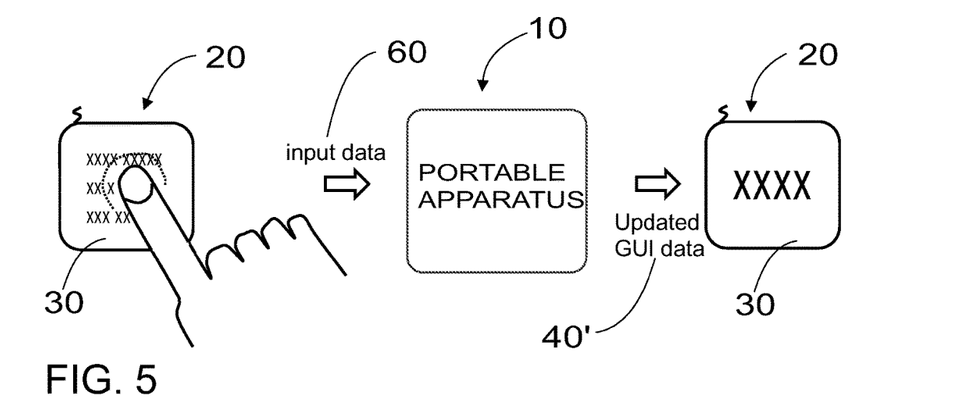
FIG. 5 illustrates entering input on an external device by a touch input.

FIG. 5 illustrates another embodiment that may be similar to that of FIG. 4 in other respects, but the portable apparatus 10 may be configured to revert a previous user interface function carried out in response to a first input data 60 received from the external device 20. The reverting may be carried out upon detecting a user input on the touch-sensitive part of the display screen 30, in other words upon receiving an earlier determined signal from the touch-sensitive part, for example. The detected user input may be a tap on the touch-sensitive part or the depression of a back button provided on the edge of the casing comprising the display screen 30 or any other suitable user input control, such as a touch screen input gesture. The tap may be provided at an arbitrary location on the touch-sensitive part of the display screen 30, i.e. the detection of the tap on any section of the touch-sensitive part causes the processing circuitry to trigger the input data to be transferred to the portable apparatus 10, which may process the input and determine updated graphical user interface data 40' affecting the user interface functionality and/or the content of the user interface if necessary based on the input data and transfer it to the external device 20 as described in connection with other embodiments.

According to an embodiment, the portable apparatus 10 may comprise a physiological sensor, such as a heart activity sensor. The processing circuitry 206 may comprise a processor and the portable apparatus 10 may further comprise a memory 210 and a communication circuitry 212 providing a wireless interface capability. The physiological sensor may be connected to a display device, such as a treadmill display or other built-in display of an exercise machine, forming the external device 20. The user interface functionality may then comprise a graphical display formed by presenting at least one graphical interaction element on the user interface and receiving user input as response to the user interacting with the graphical interaction element. The user input may preferably comprise a touch input. The user interface functionalities are transmitted from the physiological sensor 10 to the display device 20 as described in at least one embodiment of this description. The user interface functionalities may then enable the end user 100 to control, through the display device and processed in the portable apparatus, monitoring of the sensor functionality, such as heart rate, energy expenditure, heart rate ranges and/or training load. In other respects the embodiment may be similar to one or several of the other embodiments explained in this description.

According to an embodiment, the portable apparatus 10 may comprise a sports computer or a wrist unit as described above. The external device 20 may comprise a display device, such as a treadmill display or other built-in display of an exercise machine. The sports computer or the wrist unit may comprise a user interface with a display comprising at least one graphical interaction element and button and/or touch control. A user interface similar to that of the sports computer or wrist unit may be transmitted to the display device. The end user 100 may be able to provide input on the display device in a manner similar to that of the sports computer or wrist unit. The possible buttons of the wrist unit or sports computer may be represented as physical buttons or as touch screen buttons on the display device. The input data may then be transferred to the portable apparatus 10, in other words the sports computer or wrist unit, for processing. In other respects, the embodiment may be similar to one or several of the other embodiments explained in this description.

Figure 6:
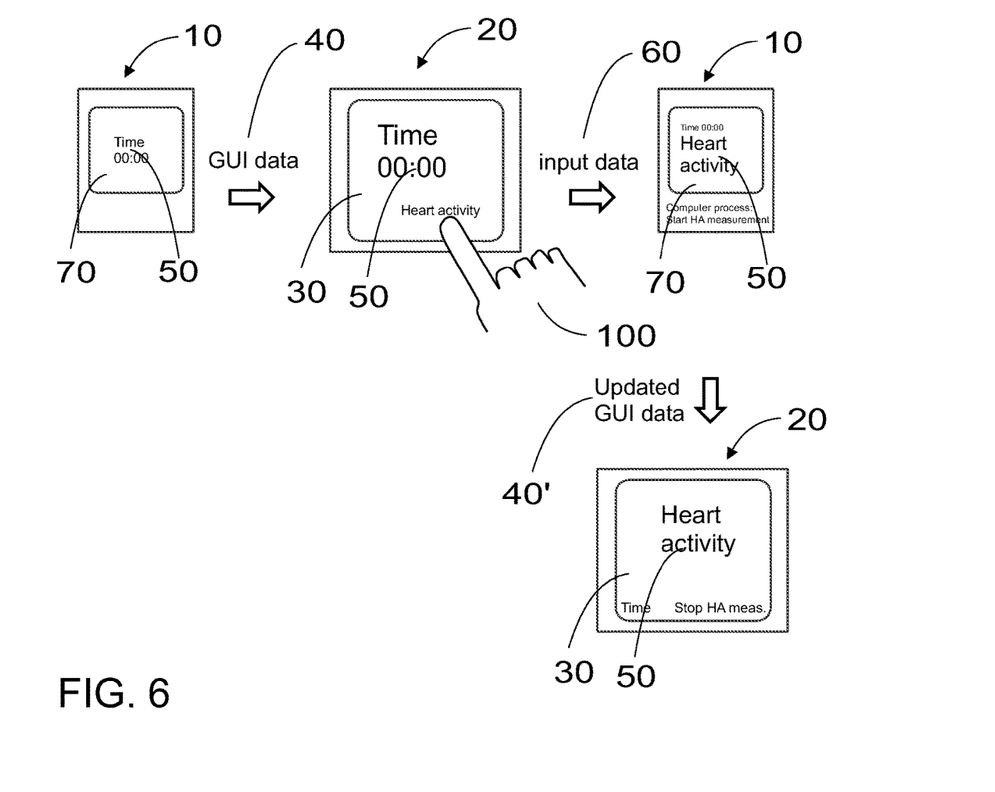
FIGS. 6, 7 and 8 illustrate schematically graphical user interface data update in different embodiments.

FIG. 6 schematically shows an embodiment, wherein graphical user interface data 40 comprising a user interface functionality, such as one presenting at least one graphical interaction element 50 in a user interface of an external device 20, is determined in the portable apparatus 10. This graphical interaction element 50 may comprise, for instance, measurement results represented on a display 30, 70. At a first moment of time, as shown on the left hand side of FIG. 6, the time may be shown in the graphical interaction element 50. Then, it may be determined in the portable apparatus 10 that graphical user interface data should be transmitted to an external device. This may take place in response to a connection being established between the portable apparatus 10 and the external device 20 or user input being received from the external device 20, for example. The graphical user interface data (GUI data) 40 determining the user interface functionality may then be transferred to the external device 20.

The graphical interaction element 50 is displayed, as a part of the user interface functionality, in the graphical user interface on the display 30 of the external device 20, illustrating the current time in this example. In this embodiment, the user interface functionality, more particularly touch screen input functionality provided on the external device 20, also comprises receiving input from the user interface. The effect of such a touch screen input may be illustrated in the user interface. In the embodiment of FIG. 6, the effect is illustrated by the smaller-sized text describing the effect of the user input, in other words changing the information displayed on the display screen 30, 70 from time to heart activity. The end user 100 uses a touch screen input gesture known as such, such as a gesture illustrated in FIG. 4 or 5. The input data 60 is transferred to the portable apparatus 10, in which it is received and processed to control a computer process relating to physiological data. Then, the updated graphical user interface data (GUI data) 40' is transmitted to the external device 20 causing the display 30 of the external device 20 to display the heart activity data instead of time. If the portable apparatus 10 also comprises a display, the same graphical interaction element 50 may be displayed on the portable apparatus display 70 as well, or a different graphical interaction element or a set of graphical interaction elements and/or display segments 50 may be displayed on the portable apparatus 10.

According to an embodiment, the portable apparatus 10 may comprise a smart phone and the external device 20 may comprise a wrist unit. The smart phone may comprise an application comprising computer program code comprising instructions comprising the steps of at least one embodiment described in this description, such as the method of FIG. 3. The user interface functionalities may provide to the end user 100, for instance, the possibility to select, on the external device, the graphical interaction element(s) and/or display segments to be displayed on the external device 20. The input data 60 may then be transferred to the portable device 10 for processing and the user interface of the external device 20 may be controlled, via the computer process and updated graphical user interface data 40', to be updated accordingly, in other words controlled to show the selected graphical interaction element(s) and/or the selected display segment. In other respects, the embodiment may be similar to one or several of the other embodiments explained in this description.

Figure 7:
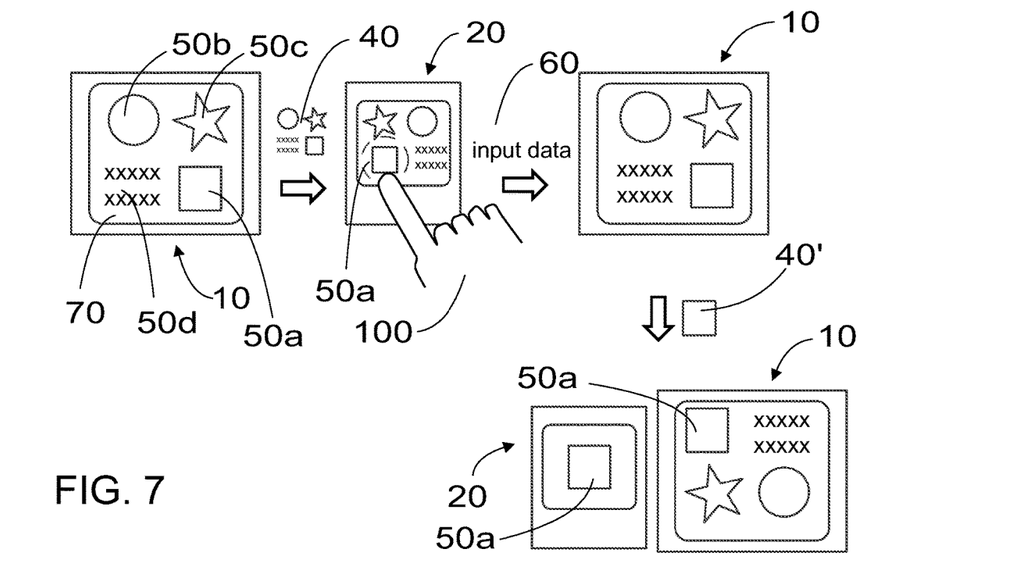

One example of such an embodiment is illustrated in FIG. 7, which may be similar to the embodiment of FIG. 6 in other respects, but wherein the graphical user interface is shown to comprise several graphical interaction elements and/or display segments 50a, 50b, 50c. The input data 60 received from the external device 20 may then affect the graphical user interfaces of both the portable apparatus 10 and the external device 20. A graphical interaction element or segment of display 50a, 50b, 50c, 50d may be selected via a user interface functionality, such as a touch screen functionality gesture, on the external device 20 by the end user 100. The input data may be transferred to the portable apparatus 10 as described above. When the input data 60 has been received and processed in the portable apparatus 10, the graphical user interface data 40 may be updated to an updated graphical user interface data 40' to be shown in the external device 20. Instead of affecting the graphical interaction element(s) shown in the portable apparatus 10 and/or the external device 20, the input data 60 may also be configured to affect the graphical user interface in another way, such as to change the position of the selected graphical interaction element or display segment on a display 30, 70. In the embodiment of FIG. 7, for instance, only the selected graphical interaction element or display segment 50a is displayed on the external device 20 and the position of the selected graphical interaction element or display segment 50a and the other graphical interaction elements or display segments 50b, 50c and 50d, respectively, are changed on the portable apparatus display 70. This may be useful if the display of the external device 20 is smaller than that of the portable apparatus 10, but easier to reach during an exercise. Thus, only the most important or topical content, such as the graphical interaction element 50a, may be shown on the external device 20. According to an embodiment, the external device 20 may be a multifunctional wrist unit, such as a so-called SMART watch, for example.

Figure 8:
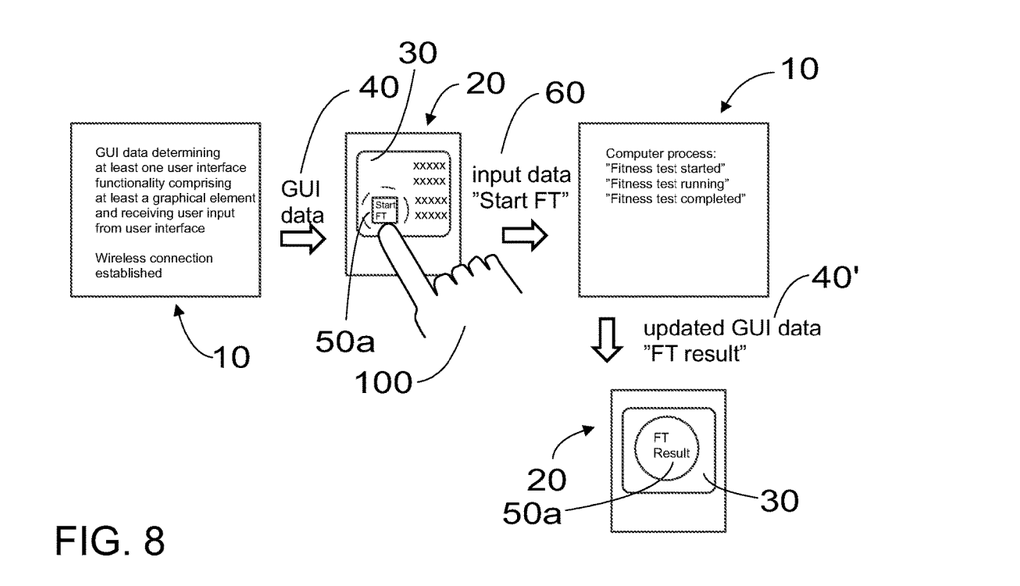

FIG. 8 schematically shows yet another embodiment, wherein graphical user interface data 40 comprising a user interface functionality, such as one presenting at least one graphical interaction element 50 in a user interface of an external device 20, is determined in the portable apparatus 10. In this embodiment, the graphical interaction element 50 is configured to represent data determined in the portable apparatus 10. In FIG. 8, the portable apparatus 10 does not comprise a display, but in different embodiments it may also comprise a display 70.

At a first moment of time, as illustrated on the left-hand side of the FIG. 8, graphical user interface data 40 is determined in the portable apparatus 10 and a wireless connection is established between the portable apparatus 10 and an external device 20. Graphical user interface data 40 is transmitted to the external device 20. The graphical user interface data 40 determines a user interface functionality comprising the graphical interaction elements to be presented in the user interface and user input to be received from the user interface. One of such graphical interaction elements, graphical interaction element 50a, presents a virtual button or icon that is configured to transmit input data 60 for starting a fitness test in response to a user input, such as the user input described in connection with FIG. 4 or 5, or another form of user input, detected on the display screen 30 on or in the vicinity of the virtual button or icon. Input data "Start FT" 60 corresponding to the user input received by the user interface functionality of the external device 20, in other words detection of the user affecting the display screen 30 of the external device 20 in a predetermined manner, is received in the portable apparatus 10. This input data 60 is then used to control a computer process, which in the embodiment illustrated in FIG. 8, means starting a fitness test, running the fitness test and completing the fitness test. The computer process may involve other devices as well, such as the accessory devices 102, 104, 108 described in connection with FIG. 1 and/or other sensors, measurement units or equipment providing physiological data, which may be utilized for acquiring physiological data related to the computer process, and additional connections to such other devices may be established as necessary, as described above. The computer process may result in updated graphical user interface data 40', which may then be transmitted to the external device 20. This may update, for instance, the content of the graphical interaction element 50a to show the fitness test result, for example.

According to an embodiment, the portable apparatus 10 comprises an audio decoder and audio playback circuitry, and the data received from the user interface by the user interface functionality and transmitted to the portable apparatus 10 may comprise control data controlling the playback and operation of the audio decoder and playback circuitry. The audio decoder may be an MPEG-1 Layer 3 (MP3) decoder, a Windows Media Audio decoder, or any other audio decoder known in the art and configured to decode and extract encoded and compressed audio tracks stored in the memory. The memory 210 storing the audio tracks may be the same physical non-volatile memory circuitry used in connection with other operations of the portable apparatus 10, or the audio tracks may be stored in an external, detachable memory unit, e.g. a memory card (SD, Memory stick, or another type of flash memory). The audio playback circuitry may include an audio signal amplifier to amplify the decoded audio tracks and an audio output interface to output the audio tracks being played. The audio output interface may be realized by wired headphone connections known in the art, and/or the audio output interface may utilize the wireless communication module to provide the audio output to Bluetooth-equipped headphones, for example. The portable apparatus 10 may also transmit audio playback information to a user interface of an external device 20, such as the wrist unit, over the wireless bidirectional connection so as to display the playback information to the user 100, and/or to other user interface devices. The playback information may include the name of an audio track currently played, an artist, playback duration (elapsed time and/or remaining time), the next song, a playlist, MP3 metadata, etc. The input data received from the graphical user interface provided on the external device 20 over the wireless connection may include input data indicating the playback of the next track, activation/disabling the music playback, volume control data, etc. Additionally, the portable apparatus 10 may include wired transferring equipment for transferring the audio tracks into the memory. Such transferring equipment may include a universal serial bus (USB) interface, for example. The USB interface may also be used for recharging a battery (not shown) of the portable apparatus 10.

A further advantage of this invention is that an interactive connection is provided at least between a portable apparatus 10 and an external device 20 wherein a graphical user interface functionality may be transferred in the form of a graphical user interface data from the portable apparatus 10 to the external device 20, and user input may be received in the form of input data from the external device 20 to the portable apparatus 10. This enables a flexible use of available display devices without the need to store and update computer program data specific to the portable apparatus 10 specific on the external device 20. Simultaneously, a graphical user interface look and feel similar to that of the end user's 100 own wrist unit or training computer may be provided, making adaptation easy for the end user 100. The end user 100 may, for instance, be able to select which graphical interaction elements are displayed on the possible display of the portable device and which on each one of the external devices 20 available.

As used in this application, the term 'circuitry' refers to all of the following: (a) hardware-only circuit implementations, such as implementations in only analogue and/or digital circuitry, and (b) to combinations of circuits and software (and/or firmware), such as (when applicable): (i) a combination of processor(s) or (ii) portions of processor(s)/software including digital signal processor(s), software, and memory (memories) that work together to cause an apparatus to perform various functions, and (c) to circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular element, a baseband integrated circuit or applications processor integrated circuit for a mobile phone or a similar integrated circuit in a server, a cellular network device, or other network device.

It should be noted that while the figures illustrate various embodiments of the portable apparatus 10 and the user interface apparatus, they are simplified block diagrams that only show some elements and functional entities, all being logical units whose implementation may differ from what is shown. The connections shown in these figures are logical connections; the actual physical connections may be different. Interfaces between the various elements may be implemented with suitable interface technologies. It is apparent to a person skilled in the art that the described apparatuses may also comprise other functions and structures. It should be appreciated that details of some functions, structures, and elements, and the protocols used for communication are irrelevant to the actual invention. Therefore, they need not be discussed in more detail herein, because such a discussion might blur the invention with unnecessary details. The implementation and features of the apparatuses according to the invention develop rapidly. This development may require additional changes to the embodiments described above. Therefore, all words and expressions should be interpreted broadly and they are intended to illustrate, not to restrict, the embodiments. Although the apparatuses have been depicted as separate single entities, different parts may be implemented in one or more physical or logical entities. It will be obvious to a person skilled in the art that, as technology advances, the inventive concept can be implemented in various ways. The invention and its embodiments are not limited to the examples described above but may vary within the scope of the claims.

The invention claimed is:

1. A wrist unit comprising:
at least one memory storing computer program code;
a communication circuitry configured to provide the wrist unit with wireless communication capability;
a user interface comprising a display that displays a parameter related to an exercise performed by a user; and
a processing circuitry configured to perform operations comprising:
providing a first user interface functionality on the user interface of the wrist unit;
determining graphical user interface data, wherein the graphical user interface data determines a second user interface functionality to be executed in a user interface of an exercise machine, wherein the second user interface functionality comprises presenting at least one graphical interaction element on the user interface of the exercise machine and receiving a user input in response to the user interacting with the graphical interaction element;
transmitting wirelessly the determined graphical user interface data to the user interface of the exercise machine to provide the second user interface functionality on the user interface of the exercise machine, wherein the first user interface functionality and the second user interface functionality are similar to each other;
receiving wirelessly input data corresponding to the user input; and
controlling a computer process relating to physiological data with the input data, wherein the input data triggers at least one of the following: starting an exercise mode, stopping an exercise mode, selecting a training program.

2. A wrist unit according to claim 1, wherein the wireless communication between the wrist unit and the user interface of the exercise machine is based on a standard WWW mark-up language.

3. A wrist unit according to claim 1, wherein the graphical interaction element represents an audio interaction.

4. A wrist unit according to claim 1, wherein the graphical user interface data further determines at least one of the following: size of the graphical interaction element, colour mode of the graphical interaction element, and position of the graphical interaction element on a display.

5. A wrist unit according to claim 1, wherein the computer process relates to at least one of the following: heart activity measurement, energy expenditure, heart rate range, and training load.

6. A wrist unit according to claim 1, wherein the processing circuitry is further configured to perform operations comprising
transferring updated graphical user interface data to the user interface of the exercise machine in response to the processed input from the graphical user interface provided using the user interface of the exercise machine.

7. A wrist unit according to claim 1, wherein a content presented on the user interface of the exercise machine is affected in response to the detection of an input on the user interface of the exercise machine, the content comprising at least one of the following: a graphical appearance of at least one graphical interaction element, a content of the graphical interaction element, a manner in which the physiological data represented by the graphical interaction element is processed, and graphical interaction element(s) and display segments to be displayed on the user interface of the exercise machine.

8. A wrist unit according to claim 1, wherein the wrist unit is configured to act as a web server providing a web-based service to which the user interface of the exercise machine may connect using internet protocol, wherein the wrist unit is further configured to establish the wireless connection between the wrist unit and the user interface of the exercise machine using internet protocol addresses.

9. A wrist unit according to claim 1, wherein the processing circuitry is further configured to perform operations comprising:
obtaining physiological data measured using at least one of the following sensors: GPS receiver, motion sensor, heart activity sensor, accelerometer, gyroscope, stride sensor, cadence sensor, magnetometer; and
wirelessly transmitting the physiological data to the user interface of the exercise machine, the transmitting causing the user interface of the exercise machine to display the physiological data.

10. The apparatus according to claim 9, wherein the processing circuitry is further configured to perform operations comprising:
processing the physiological data based on the input data received from the user interface of the exercise machine, wherein the input data affects how the physiological data displayed on the user interface of the exercise machine.

11. A computer program product embodied on a non-transitory distribution medium readable by a computer and comprising program instructions which, when executed by an apparatus, cause the apparatus to perform operations comprising:
providing a first user interface functionality on a user interface of a wrist unit;
determining graphical user interface data, wherein the graphical user interface data determines a second user interface functionality to be executed in a user interface of an exercise machine, wherein the second user interface functionality comprises presenting at least one graphical interaction element on the user interface of the exercise machine and receiving user input in response to the user interacting with the graphical interaction element and;
transmitting wirelessly the determined graphical user interface data to the user interface of the exercise machine to provide the second user interface functionality on the user interface of the exercise machine, wherein the first user interface functionality and the second user interface functionality are similar to each other;
receiving wirelessly input data corresponding to the user input; and
controlling a computer process relating to physiological data with the input data, wherein the input data triggers at least one of the following: starting an exercise mode, stopping an exercise mode, selecting a training program.

12. A method comprising:
providing a first user interface functionality on a user interface of a wrist unit;
determining graphical user interface data, wherein the graphical user interface data determines a second user interface functionality to be executed in a user interface of an exercise machine, wherein the second user interface functionality comprises presenting at least one graphical interaction element on the user interface of the exercise machine and receiving user input in response to the user interacting with the graphical interaction element;
transmitting wirelessly the determined graphical user interface data to the user interface of the exercise machine to provide the second user interface functionality on the user interface of the exercise machine, wherein the first user interface functionality and the second user interface functionality are similar to each other;
receiving wirelessly input data corresponding to the user input; and
controlling a computer process relating to physiological data with the input data, wherein the input data triggers at least one of the following: starting an exercise mode, stopping an exercise mode, selecting a training program.

13. A method according to claim 12, wherein the wireless communication between the wrist unit and the user interface of the exercise machine is based on a standard WWW mark-up language.

14. A method according to claim 12, wherein the graphical interaction element represents an audio interaction.

15. A method according to claim 12, wherein the graphical user interface data further determines at least one of the following: size of the graphical interaction element, colour mode of the graphical interaction element, and position of the graphical interaction element on a display.

16. A method according to claim 12, wherein the computer process relates to at least one of the following: heart activity measurement, energy expenditure, a heart rate range, and training load.

17. A method according to claim 12, wherein the method further comprises
transferring updated graphical user interface data to the user interface of the exercise machine in response to the processed input from the graphical user interface provided using the user interface of the exercise machine.

18. A method according to claim 12, wherein a content presented on the user interface of the exercise machine is affected in response to detection of input on the user interface of the exercise machine, the content comprising at least one of the following: a graphical appearance of at least one graphical interaction element, a content of the graphical interaction element, a manner in which the physiological data represented by the graphical interaction element is processed, and graphical interaction element(s) and display segments to be displayed on the user interface of the exercise machine.

19. A method according to claim 12, wherein the method further comprises establishing the wireless connection between the wrist unit and the user interface of the exercise machine using internet protocol addresses, wherein the wrist unit acts as a web server providing a web-based service to which the user interface of the exercise machine may connect using internet protocol.

* * * * *